United States Patent [19]

Love et al.

[11] 4,220,762

[45] Sep. 2, 1980

[54] PROCESS FOR THE PREPARATION OF CEPHAMYCIN ANTIBIOTICS

[75] Inventors: George M. Love, Mountainside; Paul Sohar, Warren, both of N.J.

[73] Assignee: Merck & Co., Inc., Rahway, N.J.

[21] Appl. No.: 25,294

[22] Filed: Mar. 30, 1979

[51] Int. Cl.$^2$ ............................................. C07D 501/20
[52] U.S. Cl. ...................................... 544/21; 424/246
[58] Field of Search .......................................... 544/21

[56] References Cited

U.S. PATENT DOCUMENTS

| | | | |
|---|---|---|---|
| 4,014,873 | 3/1977 | Christensen et al. | 424/246 |
| 4,053,286 | 10/1977 | Weinstock | 544/21 |

Primary Examiner—Nicholas S. Rizzo
Attorney, Agent, or Firm—Hesna J. Pfeiffer; Julian S. Levitt

[57] ABSTRACT

An improved process for preparing the antibiotic compound 7β-(2-thienylacetamido)-7-methoxy-3-carbamoyloxymethyl-3-cephem-4-carboxylic acid, from the N-blocked esters of the compound 7β-(D-5-amino-5-carboxyvaleramido)-3-carbamoyloxymethyl-7-methoxy-3-cephem-4-carboxylic acid (Cephamycin C), by conducting the transacylation of the latter in a homogeneous solution containing a trimethylsilyl enol ether.

3 Claims, No Drawings

PROCESS FOR THE PREPARATION OF CEPHAMYCIN ANTIBIOTICS

RELATIONSHIP TO THE PRIOR ART

The first disclosure in the patent literature of transacylation of Cephamycin C is in U.S. Pat. No. 4,014,873, issued Mar. 29, 1977. This process was conducted in the presence of a silylating agent. An improved transacylation, utilizing molecular sieves is claimed in U.S. Pat. No. 4,053,286, issued Oct. 11, 1977. The general chemistry of the transacylation reaction is in Weinstock et al., "The Chemistry of Cephamycins IV. Acylation of Amides in the Presence of Neutral Acid Scavengers", Tet. Letters, 46, 3979 (1975).

The patent, U.S. Pat. No. 4,014,873, discloses a number of silyl reagents, but not including the silyl enol ethers of this invention.

The process disclosed in that patent was primarily directed to an acylation, e.g., with thienylacetyl chloride of Cephamycin C, the latter being a fermentation product prepared from Streptomyces lactamdurans NRRL 3802, on permanent unrestricted deposit. Under certain conditions, (such as prolonging the reaction time, Col. 9, line 38), this acylation was taught to proceed in one step, see Col. 9, lines 35 to Col. 10, line 7.

SUMMARY OF THE INVENTION

It has now been discovered that using about an equivalent amount of a trimethylsilyl enol ether in the acylation reaction, a significantly higher, unexpected yield of final product can be quickly and easily recovered.

The trimethylsilyl enol ether of this invention is:

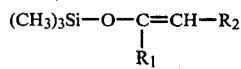  I wherein $R_1$ can be lower alkyl of 1–4 carbon atoms; $R_2$ is hydrogen or loweralkyl of 1–4 carbon atoms; or $R_1$ and $R_2$ can be a joined alkyl chain of 2–4 carbon atoms. Particularly preferred compounds are those in which $R_2$ is H and $R_1$ is $CH_3$, or 2-trimethylsiloxyl propene; or $R_1$ and $R_2$ are a joined alkyl chain of 4 carbon atoms, or 1-trimethylsiloxyl cyclohexene.

These trimethylsilyl enol ethers of Formula I are made by reacting an appropriate ketone

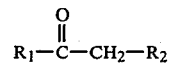

with trimethylsilyl chloride in the presence of base, such as sodium hydride. This chemistry is in the literature, see Hudrlik A. Takacs, J. Org. Chem. 43, 3861 (1978).

The crux of this invention is the recognition that from about 0.8 to about 4 equivalents of the trimethylsilyl enol ether, relative to Cephamycin C starting material is the optimal level to produce the final product in high yield. Generally, the reaction is conducted at about 80°–90° C., preferably 85° C., so that the internal pressure of reaction is about 30–45 psig., preferably about 40 psig. The reaction progress is monitered by liquid chromatographic assay of the amount of imide, or Cephamycin C having an thienylacetyl side chain at the 7-amino group in addition to its normal adipoyl group. When the imide level is at 2–5% the reaction is essentially complete (the theoretical level of 0% is probably reached, but is difficult to measure accurately); the reaction is then cooled quickly to from about 85° C. to about −10° C., in order to quench. The final product is then recovered. Generally, this reaction takes place in from 2–10 hours.

Although this reaction is best illustrated in the reaction of thienylacetyl chloride with Cephamycin C, a more generalized scheme is possible. Any acyl group of a 7-acylamido cephalosporin can be exchanged for another. The groups and definitions of breadth of this reaction are all those of U.S. Pat. No. 4,014,873, the contents of which are incorporated by reference.

A preferred embodiment is illustrated in the following flow sheet.

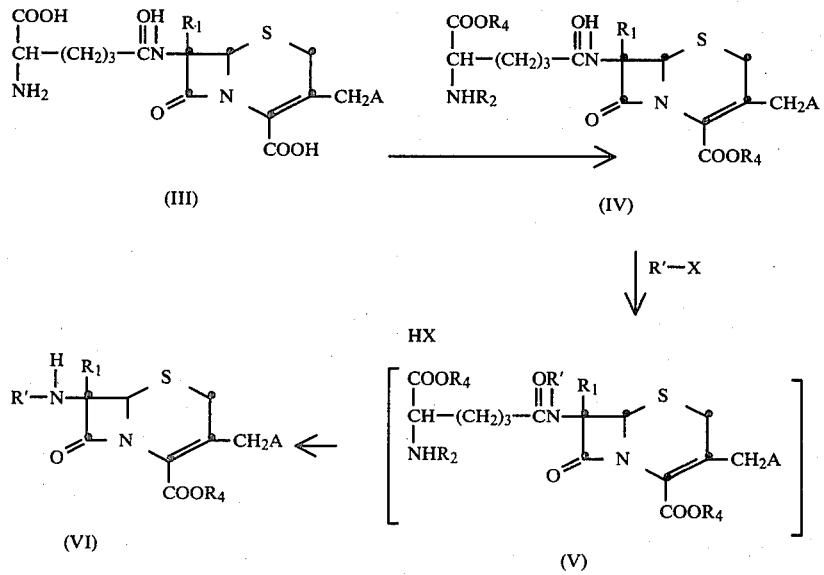

In the formulas of the above flowsheet, $R_1$ represents hydrogen or methoxy; A is as defined above, most desirably, acetoxy or carbamoyloxy; R' represents an acyl group as defined above; $R_4$ represents hydrogen or a blocking or protecting substituent; and $R_2$ represents hydrogen or an amino blocking or protecting substituent.

The side chain amino protecting group, $R_2$, in compound (V) does not have to be easily removable since the side chain is removed in the transacylation process. In fact, it is preferred that the side chain amino protecting group be one that is not easily removed since these are usually less expensive and more stable to handling during manufacturing.

In accordance with this process, the amino group of the starting cephalosporin compound (III) is first blocked ($R_2$) by reaction with a suitable reagent to protect the 5'-amino-substituent of the aminoadipoyl side chain. Thus, the amino group is blocked by amino protecting groups such as acyl, aroyl, alkoxycarbonyl, alkylsulfonyl, arylsufonyl, and the like in accordance with methods well known in this art. Specific groups suitable for blocking the amino group that might be mentioned are those wherein $R_2$ is trichloroethoxycarbonyl, tertiary butoxycarbonyl, benzoylmethoxycarbonyl, trimethylsilyl, p-methoxybenzyloxy, 2-nitrophenylsulfenyl, 2,4-dinitrophenylsulfenyl, chloroacetyl, p-nitrophenylthio, p-nitrobenzensulfonyl, p-toluenesulfonyl, methanesulfonyl, benzoyl, p-chlorobenzoyl, p-nitrobenzoyl, toluoyl, and the like, although we genenerally prefer to utilize the p-toluenesulfonyl or benzoyl derivative which is conveniently prepared by reacting the cephalosporin compound with p-toluenesulfonyl chloride of benzoyl chloride while keeping the pH of the mixture basic, i.e., between 9 and 10.

It is generally preferred to carry out the above-described reactions with a cephalosporin compound, (IV), wherein the carboxy groups on the aminoadipoyl side chain, and at the 4-position are likewise blocked or protected since maximum yields of the desired product are obtained with such derivatives. Although the carboxy group on the aminoadipoyl side chain is not necessarily deblocked, since it is removed in the cleavage step, the blocking or protecting group $R_4$ at the 4-position is preferably one which can be removed easily to obtain the free acid without disruption of the $\beta$-lactam group since the cephalosporin compounds are usually used in the form of salts such as alkali metal salts or an amine salt. Protecting groups suitable for this purpose are well known in this art. The methoxymethyl group is particularly preferred. In a preferred embodiment of the invention, the methoxymethyl group is cleaved by mixing the products with excess water.

The protected cephalosporin compound is then reacted with an acylating agent, R'-X, in a homogenous solution in the presence of the trimethylsilyl methyl carbamate described above to obtain the diaylimide product (V). The acylating agent can be an acid halide (chloride or bromide), a functional equivalent thereof such as an acid anhydride, a mercaptide, a mixed acid anhydride with other carboxlic acids, an activated ester of the carboxylic acid such as the p-nitrophenyl ester, and the like. Thienylacetyl chloride is preferred.

The acylating agent is employed in amounts in molecular excess of that of the starting cephalosporin, preferably from 1 to 6 times as much acylating agent as cephalosporin, preferably in the range of 1 to 4 molar excess or most preferably in the range of 2 to 4 molar excess.

The trimethylsilyl enol ether is used in an amount from about 0.8 to 4 equivalents to the starting cephalosporin IV.

The acylation reaction takes place in a suitable solvent medium. The temperature at which this reaction is carried out is preferred to be from about 50° C. to 90° C. Various solvents which do not contain an active hydrogen such as chloroform, acetonitrile, methylene chloride, dioxane, benzene, halobenzene, carbon tetrachloride, 1,2-dichloroethane, and diethylether are most suitable as medium for the reaction mixture. The preferred solvent is methylene chloride. If desired, the reaction mixture is kept in motion by stirring or agitating during the reaction.

The cleavage to final product VI, under the conditions of solvent, temperature, amount of trimethylsilyl enol ether, takes place spontaneously, due to liberation of acid from the reaction mixture products. The progress of reaction is monitored by decreased amounts of imide V, using standard liquid chromatographic or UV techniques. Generally, the reaction is completed within 2–10 hours, as evidenced by a drop in imide level to less than 5%.

This invention is illustrated by the following examples.

Example 1

500 ml of a methylene chloride concentrate (dried to a Karl Fischer analysis of 0.08 g) of dimethoxymethyl ester of 7$\beta$-(D-5-tosylamino-5-carboxylvaleramido)-3-carbamoyloxymethyl-7-methoxy-3-cephem-4-carboxylic acid (54.4 mmoles) 15.2 ml (13.2 g, 81.6 mmoles, if pure) of 2-trimethyl-siloxyl cyclohexene, and 27.2 ml (34.9 g, 217 mmoles, 4 eq. ) of thienylacetyl chloride were sequentially charged to a 1l. stirred autoclave and heated to 85° C. to afford an internal pressure of 40 psig. Samples were withdrawn at hourly intervals and assayed by lc.

| Hour | Sym Imide | lc mole % Thienyl Product MM | Unsym. Imide | Thienyl Product Anhy |
|---|---|---|---|---|
| 1 | 13.1 | 42.2 | 30.9 | — |
| 2 | 16.7 | 61.3 | 12.4 | — |
| 3 | 9.3 | 72.3 | 5.5 | — |
| 4 | 0.5 | 79.4 | 0.2 | 2.4 |

| Hour | Starting Material MM | Mass Bal. | Total Imide |
|---|---|---|---|
| 1 | 24.5 | 111 | 44 |
| 2 | 16.7 | 107 | 29 |
| 3 | 12.9 | 100 | 15 |
| 4 | 11.3 | 94 | 0 |

The batch was quickly cooled at exactly 4.0 hours since this appeared to be the zero imide point. After cooling to 20° C., 429 g. (33.4 mmoles) of the batch was transferred from the autoclave to a 2l. three neck flask with an overhead stirrer and cooled to −10° C. 67 ml of ethanol was added and the mixture was aged for 30 minutes followed by the addition 670 ml of room temperature water. The pH of the two phase mixture was adjusted to 5.0 with 1 NNaOH solution, and the methylene chloride was removed under reduced pressure.

The two phase mixture was vigorously stirred overnight at 22° C. while the pH was held at 5.0 by a pH meter switched pump which added 1 NNaOH solution as necessary to hold this pH. The crude mixture was then sequentially extracted 3 times at pH's of 4.4, 3.8 and 3.5 with 350 ml of methylene chloride. Lc assay of the 958 ml aqueous layer after the third extraction, column feed, was 11.55 g/l indicating a yield of 77.5%, as the carboxylic acid.

Isolation

After standing overnight at 6° C., the assay of the column feed had fallen from 11.55 g/l to 11.17 g/l. The column feed was then isolated using an IRA-68 chloride cycle resin column, followed by concentration using an XAD-2 resin column which was eluted with ethyl acetate. A breakthrough of 2.9% occurred on the IRA-68 column. Disregarding this breakthrough, the yield to ethyl acetate rich cut was 91.5%, and the overall yield to final product free acid hydrate was 88% with 2.2% in the mother liquors. Final product assays are given below.

| | |
|---|---|
| 1 c uncorrected purity, | 93.0% |
| EtOAc | 0.4% |
| HoAc | 0.34% |
| EtOH | 0.003% |
| KF | 4.89% |

EXAMPLE 2

Using a similar procedure to Example 1, except using 1-trimethylsiloxyl propene instead of 2-trimethylsiloxyl cyclohexene, a yield of 74.0% was achieved in the column feed.

Having fully described this invention, what is claimed is:

1. In the process of preparing the compound

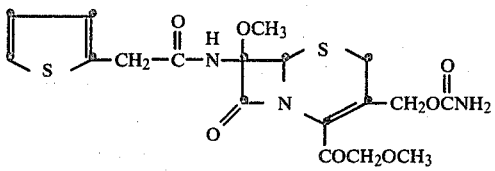

by reacting thienylacetyl chloride with

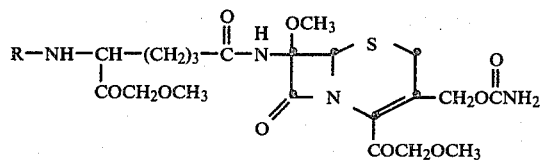

wherein R is p-tosyl in an inert solvent such as methylene chloride at a temperature of between 50°-90° C., the improvement comprising carrying out the reaction in the presence of about 0.8 to 4 equivalents of trimethylsilyl enol ether $$(CH_3)_3Si-O-\underset{R_1}{C}=CH-R_2 \qquad I$$

wherein $R_1$ can be lower alkyl of 1-4 carbon atoms; $R_2$ is hydrogen or loweralkyl of 1-4 carbon atoms; or $R_1$ and $R_2$ can be a joined alkyl chain of 2-4 carbon atoms; for a time sufficient to reduce the intermediate imide level to less than 5%, then quenching by cooling to between 20° C. and −10° C., and recovering the product thereby produced.

2. The process of claim 1 in which the trimethylsilyl enol ether is 2-trimethylsiloxyl propene.

3. The process of claim 1 in which the trimethylsilyl enol ether is 1-trimethylsiloxyl cyclohexene.

* * * * *